United States Patent

Miller et al.

[11] Patent Number: 6,063,146
[45] Date of Patent: May 16, 2000

[54] ETHERCARBOXYLIC ACIDS AS ASPHALTENE DISPERSANTS IN CRUDE OILS

[75] Inventors: Dennis Miller, Kelkheim; Axel Vollmer, Kriftel; Michael Feustel, Köngernheim; Peter Klug, Grossostheim, all of Germany

[73] Assignee: Clariant GmbH, Frankfurt, Germany

[21] Appl. No.: 09/114,605

[22] Filed: Jul. 13, 1998

[30] Foreign Application Priority Data

Jul. 14, 1997 [DE] Germany .......................... 197 30 085

[51] Int. Cl.$^7$ ...................................................... C10L 1/18
[52] U.S. Cl. ................. 44/437; 44/443; 44/447; 208/48 AA
[58] Field of Search .............................. 44/385, 437, 443, 44/447; 208/48 AA

[56] References Cited

U.S. PATENT DOCUMENTS

| | | | |
|---|---|---|---|
| 2,807,525 | 9/1957 | Foreman | 44/443 |
| 3,920,414 | 11/1975 | Steere et al. | 44/447 |
| 4,414,035 | 11/1983 | Newberry et al. | 134/3 |
| 4,464,182 | 8/1984 | Tack et al. | 44/443 |
| 4,722,396 | 2/1988 | Balzer | 166/274 |
| 5,021,498 | 6/1991 | Stephenson et al. | 524/484 |
| 5,114,616 | 5/1992 | Kupfer et al. | 252/337 |
| 5,143,594 | 9/1992 | Stephenson et al. | 208/48 |
| 5,250,203 | 10/1993 | Denis et al. | 568/517 |

FOREIGN PATENT DOCUMENTS

| | | |
|---|---|---|
| 2029465 | 5/1991 | Canada . |
| 2075749 | 2/1993 | Canada . |
| 0207312 | 1/1987 | European Pat. Off. . |

OTHER PUBLICATIONS

D.L. Chang and H.S. Fogler (SPE paper No. 25185, 1993).
M.N. Bouts et al. (J. Pet. Technol. 47, 782–7, 1995).
European Search Report, Nov. 27, 1998.

*Primary Examiner*—Gabrielle Brouillette
*Assistant Examiner*—Cephia D. Toomer
*Attorney, Agent, or Firm*—Miles B. Dearth

[57] ABSTRACT

The present invention relates to crude oils and products derived therefrom comprising, as asphaltene dispersant, ethercarboxylic acids of the formula $$RO(CH_2CHR_1O)_x(CH_2CHR_2O)_yCH_2-CO_2H$$

where the substituents have the meaning defined in the description.

5 Claims, No Drawings

ETHERCARBOXYLIC ACIDS AS ASPHALTENE DISPERSANTS IN CRUDE OILS

Asphaltenes are constituents of crude oils. They comprise a multiplicity of structures, particularly high-molecular-weight condensed aromatic components containing heteroatoms. In view of the complexity of their chemistry, asphaltenes are described as the oil fraction which is soluble in benzene, but is insoluble in n-pentane.

Asphaltenes are usually present in crude oil as a colloidal dispersion. These are stabilized by oil resins.

Asphaltenes can precipitate out during the production, refining, transport and storage of crude oil and products derived therefrom, such as heavy fuel oil or marine oil. Shared causes for this precipitation are a decrease in temperature or a change in composition (e.g. evaporation of readily volatile constituents). Asphaltenes can also precipitate out during flow through porous media. Flooding with $CO_2$ during the transport process can cause asphaltenes to flocculate or to precipitate.

Some oils comprise hydrocarbon waxes which precipitate out at low temperatures. Interactions between the precipitation of wax and asphaltenes can increase the total amount of precipitated substance or their rate of formation.

Precipitated asphaltenes cause problems in the production and processing of crude oils. Asphaltenes precipitate in valves, pipes and transport equipment. On hot surfaces, such as heat exchangers, the carbonization of these precipitates can make their removal very difficult. The precipitates reduce the efficiency of plants and, in the worst case, can lead to a complete blockage and to a production stoppage, which causes high costs.

Heavy oils which are often used for marine propulsion, comprise considerable amounts of asphaltenes. The precipitation of asphaltenes can lead both to poor combustion and also difficulties in the handling and storage of the engine fuel.

Bitumen, heavy oils and residues are sometimes diluted with solvent to decrease the viscosity for transport. If asphaltenes precipitate out in the course of this, problems in handling result from this.

The precipitation of asphaltenes can be prevented or decreased by small amounts dispersants. These substances have one or more of the following effects:
a) the amount of precipitate is decreased;
b) the precipitate forms more slowly;
c) the precipitate is more finely distributed; and
d) the tendency of the precipitate to accumulate on surfaces is decreased.

If precipitate of asphaltenes have already formed, they can be removed by the use of solvents. The addition of a dispersant can improve the efficiency of these solvents.

A multiplicity of asphaltene dispersants are already known. CA 2 029 465 and CA 2 075 749 describe alkylphenol-formaldehyde resins in combination with hydrophilic-lipophilic vinyl polymers. The asphaltene-dispersing properties of dodecylbenzenesulfonic acid have been described in U.S. Pat. No. 4,414,035, and in addition by D. -L. Chang and H. S. Fogler (SPE paper No. 25185, 1993) and by M. N. Bouts et al. (J. pet. Technol. 47, 782–7, 1995).

The dispersants disclosed to date can only partly solve the problems caused by the precipitation of asphaltenes. Since oils vary in their composition, individual dispersants can only act effectively in a limited range. Sometimes, even small changes in oil composition have a great effect on the dispersion properties for asphaltenes. Therefore, in some cases, the known dispersants are not satisfactory and additional types are required.

The object was thus to provide novel asphaltene dispersants which do not have the disadvantages described of the dispersants known to date.

SUMMARY OF THE INVENTION

Surprisingly, it has been found that ethercarboxylic acids of the formula

can be used to prevent the precipitation and/or the deposition of asphaltenes in crude oils and products derived therefrom.

The invention thus relates to crude oils and products derived therefrom comprising, as asphaltene dispersant, ethercarboxylic acids of the formula

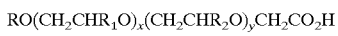

where
R is $C_6$–$C_{22}$-, preferably $C_9$–$C_{18}$-alkyl or -alkenyl, $C_6$–$C_{20}$-alkylaryl,
$R_1$ and $R_2$ independently of one another are H or methyl, preferably H, and
x and y independently of one another are a number from 0 to 20, the total of x and y being 1 to 20, preferably 1.5 to 8.

Products derived from crude oils are, for example, heavy fuel oil, marine oil or bitumen.

DESCRIPTION OF THE PREFERRED EMBODIMENTS

The ethercarboxylic acids according to the invention can, in addition to other methods, be prepared by reacting alkylphenol or fatty alcohols of natural or synthetic origin with ethylene oxide and/or propylene oxide to give the corresponding alkoxylated alcohols and subsequently reacting with alkali (sodium hydroxide, potassium hydroxide) and sodium chloroacetate or chloroacetic acid derivatives; to isolate the ethercarboxylic acids, the mixture is then acidified and the ethercarboxylic acid is separated from the salt-containing water phase.

The products thus obtained are mixtures of molecules having different lengths of poly(alkylene oxide) chains. The numbers x and y are therefore to be understood as means.

Suitable products for the dispersion of asphaltenes are both pure ether carboxylic acids and their technical-quality grades which, in addition to ether carboxylic acids (in amounts >50%, preferably 60–90%) usually also comprise the underlying alkoxylated alcohol (in amounts of 140%, preferably 5–30%) and water (in amounts <20%, preferably 2–10%). The ethercarboxylic acids mentioned in the examples are technical-quality grades of this type which comprise between 60 and 80% pure ethercarboxylic acid.

The dispersant according to the invention is used at a concentration of 0.5 to 10,000 ppm, preferably 2 to 2000 ppm.

For easier dosing, the dispersant can be formulated as a solution in an oil-miscible solvent, such as aromatic hydrocarbons or mixtures of hydrocarbons and an aliphatic alcohol.

In addition to the dispersant according to the invention, alkylphenol-formaldehyde resins, alkoxylated amines, wax dispersants or any mixtures thereof can also be used.

Likewise, other organic acids having surfactant properties, such as mono- or dialkylbenzenesulfonic acids, petroleum sulfonic acids and alkanesulfonic acids, can also be used as additional components.

Testing the efficiency of asphaltene dispersants

Principle of the dispersion test

The dispersion or precipitation of asphaltenes depends on the nature of the hydrocarbon medium. Asphaltenes are soluble in aromatic, but not aliphatic, hydrocarbons. Thus dispersants can be tested by dissolving the oil or extracted asphaltenes in an aromatic solvent and by then adding an aliphatic hydrocarbon in order to produce a precipitate. Since asphaltenes have a darker color, the extent of the precipitate can be determined by colorimetric measurement of the supernatant liquid. The darker the supernatant liquid, the more asphaltenes remain dispersed, that is the better is the dispersant. This test is described in CA 2 029 465. In our version of the test, the precipitant medium is selected in such a manner that the majority, but not all, of the asphaltenes are precipitated.

Procedure for the dispersion test a) A 25% strength oil solution in toluene is filtered to remove impurities;

b) introduce 9.5 ml of heptane as precipitant for asphaltenes and 0.5 ml of toluene/dispersant mixture (25:1) into a graduated glass tube with a good 10 ml capacity and shake well. This corresponds to a dispersant concentration of 2000 ppm. If necessary, the amount of dispersant can be varied. Use pure toluene for the blank samples;

c) then add 0.1 ml of the filtered oil solution to the glass tube and likewise shake well;

d) allow the entire mixture to stand for 2 hours free from vibrations. The precipitated asphaltenes should be allowed to collect at the bottom of the tube;

e) at the end of this time, estimate the volume of sediment by means of the graduation, record the appearance of the entire sample and then carefully take up 1 ml of the supernatant phase using a pipette;

f) dissolve the amount drawn off in 5 ml of a 99:1 toluene/triethanolamine mixture and analyze it photometrically at 600 nm.

Evaluation of the dispersion test

The following expression is used as a relative measure of dispersion $$A = 100(D-D_0)/D_0,$$

where $D$ and $D_0$ are the optical density of test solution and blank sample. The maximum attainable value of A, $A_{max}$, corresponds to complete dispersion of the asphaltenes. It can be estimated by carrying out an experiment without dispersant, using toluene instead of heptane—this leaves the asphaltenes completely dispersed. The volume of sediment gives further information on the efficacy of the dispersant.

The smaller the amount of sediment, the better is the substance dispersed.

EXAMPLES

Substances according to the invention were tested by the dispersion test using an asphaltene-rich oil from Venezuela. The dose was 2000 ppm.

| No. | R | $R_1$ | x | y | Dispersant action A [%] | Sediment volume ml |
|---|---|---|---|---|---|---|
| 1 | Oleyl | H | 2 | 0 | 108 | 0 |
| 2 | $C_{14}/_{15}$Alkyl | H | 3 | 0 | 110 | 0 |
| 3 | $C_{14}/_{15}$Alkyl | H | 7 | 0 | 106 | 0 |
| 4 | $C_{12}$Alkyl | H | 3 | 0 | 112 | 0 |
| 5 | i-$C_9$Arylalkyl | H | 4 | 0 | 115 | 0 |
| Blank sample | — | — | — | — | 0 | 0.45 |

In this experimental series, the maximum dispersant action $A_{max}$ was approximately 120%.

What is claimed is:

1. A composition comprising crude oil, heavy fuel oil, marine oil or bitumen and as an asphaltene dispersant, an ethercarboxylic acid of the formula $$RO(CH_2CHR_1O)_x(CH_2CHR_2O)_yCH_2—CO_2H$$

where

R is $C_6$–$C_{22}$-alkyl or -alkenyl, $C_6$–$C_{20}$-alkylaryl, $R_1$ and $R_2$ independently of one another are H or methyl, and x and y independently of one another are a number from 0 to 20, the sum of x and y being 1 to 20.

2. A composition as claimed in claim 1, wherein

R is $C_9$–$C_{18}$-alkyl or -alkenyl, $C_6$–$C_{20}$-alkylaryl, $R_1$ and $R_2$ are H and x and y independently of one another are a number from 0 to 20, the sum of x and y being 1.5 to 8.

3. A process for dispersing asphaltenes in crude oil, heave fuel oil, marine oil or bitumen compositions, which comprises adding ethercarboxylic acids as claimed in claim 1 to said compositions in an amount of from 0.5 to 10,000 ppm.

4. The process as claimed in claim 3, wherein further comprising adding said compositions, alkyl-phenol-formaldehyde resins, alkoxylated amines, mono- or dialkyl-sulfonic acids, petroleum sulfonic acids, alkanesulfonic acids, wax dispersants or any mixtures thereof.

5. The process of claim 3 wherein said ethercarboxylic acid is added in an amount of from 2 to 2000 ppm.

* * * * *